United States Patent [19]
Safir

[11] Patent Number: 4,799,784
[45] Date of Patent: Jan. 24, 1989

[54] VISUAL VERTEX FINDER

[76] Inventor: Aran Safir, 3 Ellsworth Ave., Cambridge, Mass. 02139

[21] Appl. No.: 877,265

[22] Filed: Jun. 23, 1986

[51] Int. Cl.$^4$ ............................ A61B 3/00; A61B 3/10
[52] U.S. Cl. .................................. 351/212; 351/246; 351/219
[58] Field of Search ............... 351/212, 246, 247, 219, 351/221, 205; 128/303.17, 303 R, 305

[56] References Cited

U.S. PATENT DOCUMENTS 4,265,519 5/1981 Pomerantzeff .
4,669,837 6/1987 Schirmer et al. .

OTHER PUBLICATIONS

"Measurement of Visual Axis Using a Laser Beam", *Advances in Diagnostic Visual Optics*, Hiroshi Vozato et al, pp. 22-28.

"The Operating Microscope, III. Accessories", Peter Hoerenz, Dipl. Ing. Phys., *Journal of Microsurgery*, pp. 22-26, Sep. 1980.

"The New Weck Surgical Microscopes", Edward Weck & Co., Inc., Weck Drive, P.O. Box 12600, Research Triangle Park, NC 27709.

"Comparison...", by Steinberg et al, *American Journal of Ophthamology*, pp. 605-608, Nov. 1983.

*Primary Examiner*—Rodney B. Bovernick
*Assistant Examiner*—Jay Ryan
*Attorney, Agent, or Firm*—Weingarten, Schurgin, Gagnebin & Hayes

[57] ABSTRACT

An instrument and technique is disclosed for locating the exit point of the visual axis at the corneal surface. Several methods are described. One includes an optical device movable on the corneal surface and being partially reflective and transparent to incident light. A collimated light beam is directed along the axis through the device onto the retina of a patient's eye, and a viewing means is provided for observing a light beam reflected from the device along the incident axis when the eye fixates on the collimated beam. The invention can also be implemented for direct visualization without the optical device, by off-axis viewing of scattered light produced by the incident collimated beam impinging on the corneal tissue, or by viewing fluorescent radiation from the point of intersection of the incident beam produced by a fluorescent dye applied to the cornea.

20 Claims, 2 Drawing Sheets

VISUAL VERTEX FINDER

FIELD OF THE INVENTION

This invention relates generally to physiological optics, and more particularly to an instrument and technique for locating and marking a reference point on the corneal surface of the human eye.

BACKGROUND OF THE INVENTION

Restorative surgery of the optical system of the eye has progressed to a new era with the advent of microsurgical techniques which allow finer and more precise operations than were previously attempted. As a consequence, the details of physiological optics have become especially important to corneal surgery.

For example, in current refractive keratoplasty procedures, the operation alters the optical characteristic of the central part of the cornea, and therefore the surgery must be done in precisely the correct location. Otherwise, the optimum therapeutic effect is degraded. Failure to place the surgical site correctly results in impaired visual acuity or other serious symptoms. There are no appropriate instruments that accurately locate and mark a surgical reference point about which the incisions can be made. Many consider the exit point of the visual axis (the point where the axis from the fovea, to the point of fixation, pierces the corneal surface) to be the ideal reference point. However, none of the instruments and techniques presently available accurately locates that point.

In the present state of the art, there is controversy on where the actual exit point of the visual axis lies and, accordingly, on what constitutes the best methodology for locating it. Some studies regard the pupillary center as the appropriate point of exit of the visual axis. (Enoch, J. M., and Laties, A. M.: "An Analysis of Retinal Receptor Orientation, II. Predictions for Psychophysical Tests", *Invest. Ophthalmol.*, 10:959, 1971). There are practitioners who therefore advocate locating and marking the pupillary center while viewing the pupil coaxially with the point of fixation. (Walsh, P. M. and Guyton, D. L., "Correspondence", *Am. J. Ophthalmol*, 97:5, 1984). In contrast, there are other practitioners who have relied on an operating microscope, having a fiberoptic probe or other light source associated with one of the two microscope objective lenses to simultaneously illuminate and view the cornea. The reflected image of the light source as it reflects from the corneal surface (a point known as the corneal reflex), as the patient fixates on the source, is thereupon marked with a needed as the reference point. (Steinberg, E. B. and Waring, G. O., "Comparison of Two Methods of Marking the Visual Axis on the Cornea During Radial Keratotomy", *Am. J. Opthalmol.*, 96:605, 1983).

These two methods for choosing the exit point of the visual axis, which represent the state of the art, are fundamentally in error and deficient in several respects.

The present techniques which make use of the corneal front surface as a mirror to produce an image of a light source as the reference point are not well founded. The corneal reflex is located on a radius of the corneal front surface, situated perpendicular to the surface at the point of reflection. If the corneal surface at that point, is not also perpendicular to the visual axis, the axis will be displaced at the surface by refractive bending. The reflected image as seen by the practitioner will then be displaced by such a tilt of the corneal surface to a false or inaccurate point. This makes the location of the corneal reflex an unreliable indicator of the point where the visual axis intersects the corneal surface.

The argument for the pupillary center is based partly on the assumption that the Stiles-Crawford Effect (SCE) shows the maximal sensitivity lobe of the fovea to be directed at the pupillary center. In reality, however, the lobe is directed only approximately at the center and may be distant from it by 1.5 mm or more in normal eyes. Surgical operations centered on the pupil of such eyes might produce significant degradation of the desired optical effect because of the false belief that the optics of the surgery were properly centered, and that scars caused by the surgery were located sufficiently far from the visual axis to create negligible light scattering or other image distortion. The utility of the pupillary center is also questionable because the pupil is frequently not circular. It is often irregular in symmetry and lacks a stationary central point during dilation and accommodation. The pupil is often induced to dilate or constrict by the application of drugs during examination or surgery. The center of the SCE sensitivity function in some subjects receiving pilocarpine to constrict the pupil has been found to be outside of a 2mm diameter circle drawn about the center of the constricted pupil. (Reference Enoch, J.M. and Hope, G.M.: "An Analysis of Retinal Receptor Orientation, IV, Center of the Entrance Pupil and the Center of Convergence of Orientation and Directional Sensitivity", *Invest. Ophthalmol.*, Vol. 11, No. 12, pp 1017–1021, 1972). Additionally, the plane of the pupil is placed well apart from the cornea. The parallactic shifts in the two planes make the location of a point on the cornea, while estimating the pupillary center, a task fraught with inaccuracy.

SUMMARY OF THE INVENTION

In accordance with the present invention, an instrument and technique is provided to accurately detect the intersection of the visual axis with the corneal surface and to mark that point of intersection.

The visual axis is made coaxial with a narrow collimated light beam directed into the eye, and the intersection of the light beam with the corneal surface is detected and marked. The point of intersection of the visual axis with the front corneal surface has no agreed-upon name in current practice, and is termed herein the "visual vertex." In one embodiment, the passage of the narrow light beam into and through the corneal tissue is viewed at a small angle to the incident beam to detect the visual vertex by scattering of the light in the tissue. In another embodiment, the corneal surface is coated with a fluorescent dye, and the radiant light beam intersecting the corneal surface is rendered visible by the fluorescent radiation of the activated dye. In a further embodiment, the narrow light beam is coaxial with an optical axis of a viewing instrument such as an operating microscope, and is directed onto the surface of a curved beam splitter disposed on the cornea. The beam splitter is manipulated on the corneal surface to a position at which the reflected beam is coincident with the visual axis as seen through the viewing instrument.

The invention avoids the inherent errors introduced by the use of the corneal surface as a mirror, and achieves precise location of the visual vertex by means which are simple in construction and easy to use.

In a presently preferred implementation of the invention employing a beam splitting device, that device comprises a base portion for engagement with the cornea of a patient's eye and having a central portion which is partially reflective and partially transmissive to the incident light beam. A handle or other means is provided for moving the device on the corneal surface to a position at which light is reflected from the central portion along the incident axis. Marking means can be provided on the device for marking the reference point. The light source producing the narrow collimated beam is preferably incorporated in the optical system of an operating microscope, or other appropriate viewing instrument, to direct the beam coincidently with an optical axis of the microscope. The light source also serves as a fixation point for the patient. This source can typically be a low-power laser, solid-state laser or light-emitting diode.

In operation, a portion of the collimated light passes through the beam splitter to the fovea of the patient's eye so that the eye of the patient may fixate on the light source. A portion of the incident light is reflected coaxially along the incident rays and is visible to the observer viewing through the microscope, when the beam splitter has been moved to its proper position. The construction of the beam splitter is such that the reflected light emanates from a virtual image point which lies directly at the intersection point on the corneal surface known as the visual vertex. This image also lies exactly at the center of the area marked by the marking means. The appearance of the image indicates that the proper positioning of the beam splitter has been achieved. The practitioner discerns the image by monitoring the placement of the beam splitter as seen through the viewing microscope or other viewing apparatus. The image thereby appears to the practitioner only when the beam splitter is positioned exactly at the visual vertex while the patient's eye fixates on the collimated light source. At no time does the device obstruct the patient's fixation on the source.

The invention can also be implemented for direct visualization without the beam splitting device. In this embodiment, the narrow beam impinging on the cornea may be coincident with the optical axis of one side of a binocular microscope, and the intercept of the impinging beam with the cornea is viewed via the other side of the microscope which is off-axis from the illuminated side by a small amount. The light is seen by reason of scattering of the impinging beam in its path through the corneal tissue. The wavelength of the incident narrow beam is determined to provide an intended degree of scattering for easy viewing, and can be, for example, a solid state laser in the blue-green or blue wavelength range. The point of impingement can be recorded with any suitable marking apparatus. The incident beam can impinge on a fluorescent dye applied to the cornea, and the fluorescent radiation thereby produced can be viewed through the microscope to detect the visual vertex.

DESCRIPTION OF THE DRAWINGS

The invention will be more fully understood from the following detailed description taken in conjunction with the accompanying drawings, in which.

DETAILED DESCRIPTION OF THE INVENTION

Figure 1:
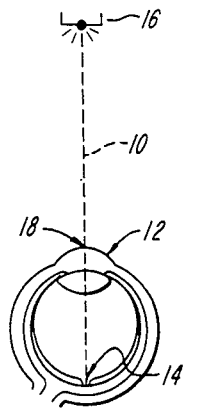
FIG. 1 is a sectional schematic view of the orientation of the eye in fixation upon a collimated light source according to the invention.

The human eye is schematically shown in FIG. 1. The visual axis 10 is the axis through the cornea 12 between the fovea 14 and a fixation point 16 upon which the eye of the patient is fixated. The visual axis is shown for simplicity as a straight line. In actuality this axis is not necessarily straight, since if it is not perpendicular to the corneal surface at the visual vertex 18, it will be bent by refraction. The visual vertex 18 is the point of interaction of the visual axis with the corneal surface and which is detected and marked in accordance with this invention.

Figure 2:
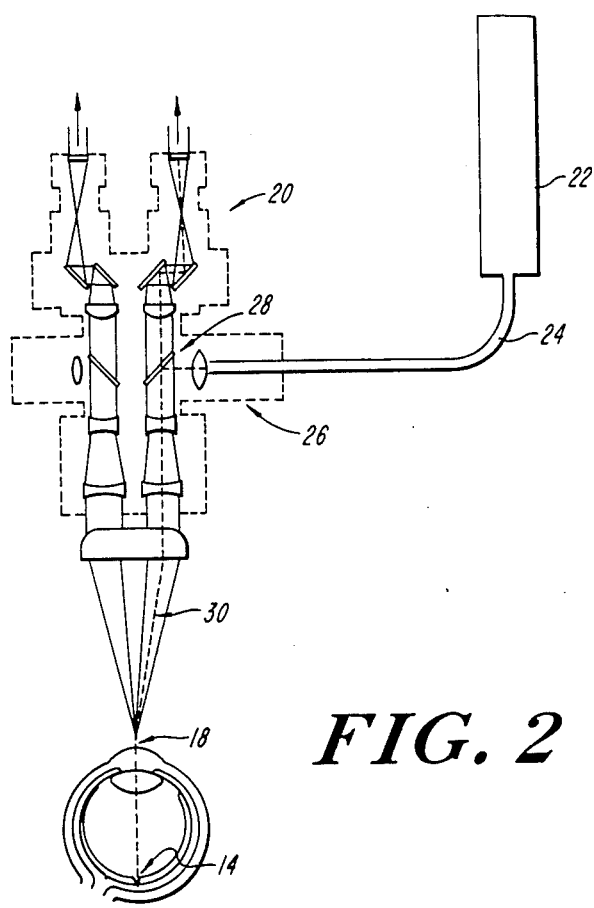
FIG. 2 is a diagrammatic view of a viewing instrument according to the present invention.

In the illustrated embodiment, the narrow beam of light is introduced into the eye and viewed by the apparatus 20 of FIG. 2 which can be a binocular operating microscope or slit lamp. The collimated light source 22 may be a lowpower laser or light-emitting diode (LED), and the narrow collimated beam is coupled through an optical fiber or bundle 24 to a coupler 26 which includes a beam splitter 28 in one of the binocular paths. A collimated beam is thereby directed along the axis 30 of the microscope coincident therewith. The optical configuration of this apparatus allows the practitioner to detect the intersection of the incident beam with the corneal surface to precisely detect the visual vertex.

Figure 3:
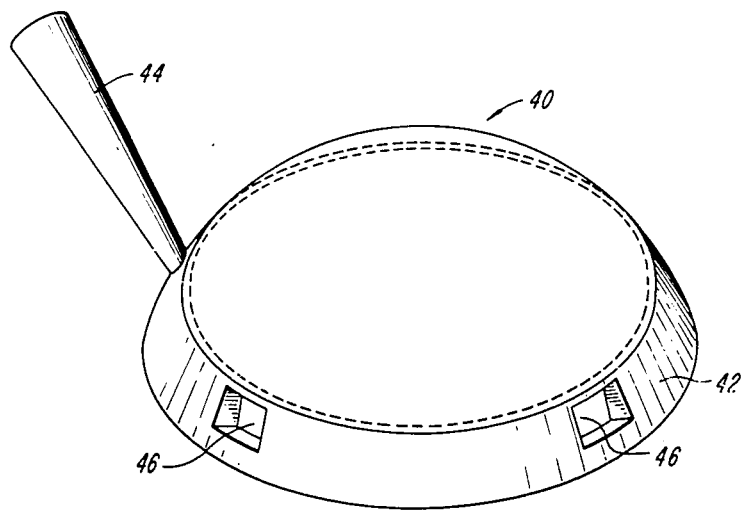
FIG. 3 is a pictorial view of a beam splitter according to the present invention.

The viewing instrument can be advantageously employed with the curved beam splitter 40 shown in FIG. 3, and which includes a bezel 42 for support of the device on the corneal surface 12, and a handle 44 for manipulation of the device along the surface 12. Scuppers 46 are provided through the bezel 42 to prevent the accumulation of moisture or fluid by allowing such to pass through the scupper openings. The interior of the device is thereby kept free from the optically degrading effects of liquid which might otherwise collect within.

Figure 4:
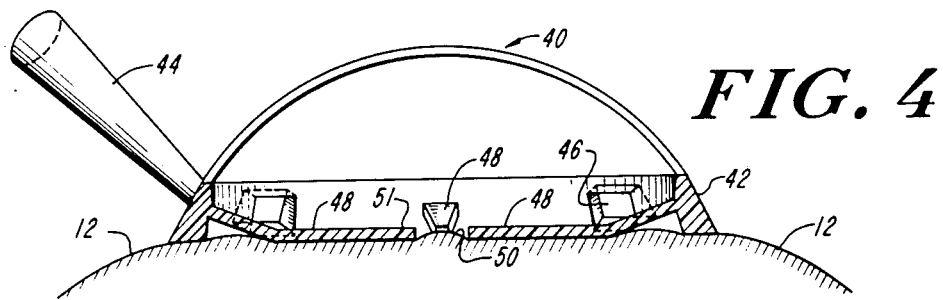
FIG. 4 is a sectional elevational view of the embodiment of FIG. 3.
Figure 5:
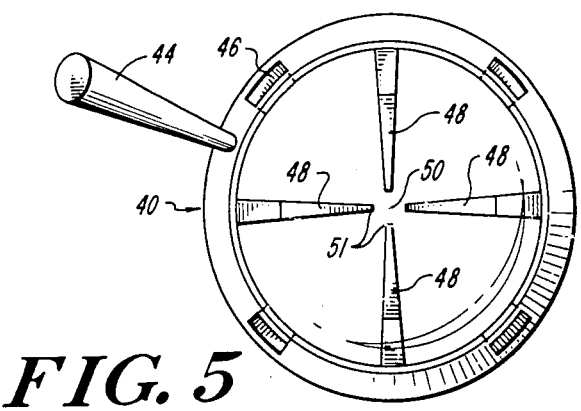
FIG. 5 is an elevated axial view of the embodiment of FIG. 3.

The cross section and construction of the beam splitter 40 is shown in FIG. 4. Projecting from the inner circumference of the bezel 42 are a plurality of radial spokes 48 which extend from the bezel inward to the secondary focus 50 of the beam splitter. The tips 51 of the spokes 48 do not occlude the focus 50 of the beam splitter when viewed axially, as shown in FIG. 5. The tip pattern of the spokes 48 serve to define the focus 50 of the beam splitter, and the visual vertex within the focal area. Additionally, the spokes 48 are aligned parallel to the plane of contact between the edge of the bezel 42 and the corneal surface 12. The depth of the spokes 48 is further aligned so as to impress, to a depth sufficient to create an indentation in the corneal surface 12 when the beam splitter 40 is pressed upon the surface 12. The alignment and depth of the spokes is sufficient to cause indentations of the corneal surface which remain visible upon removal of the device 40.

Figure 6:
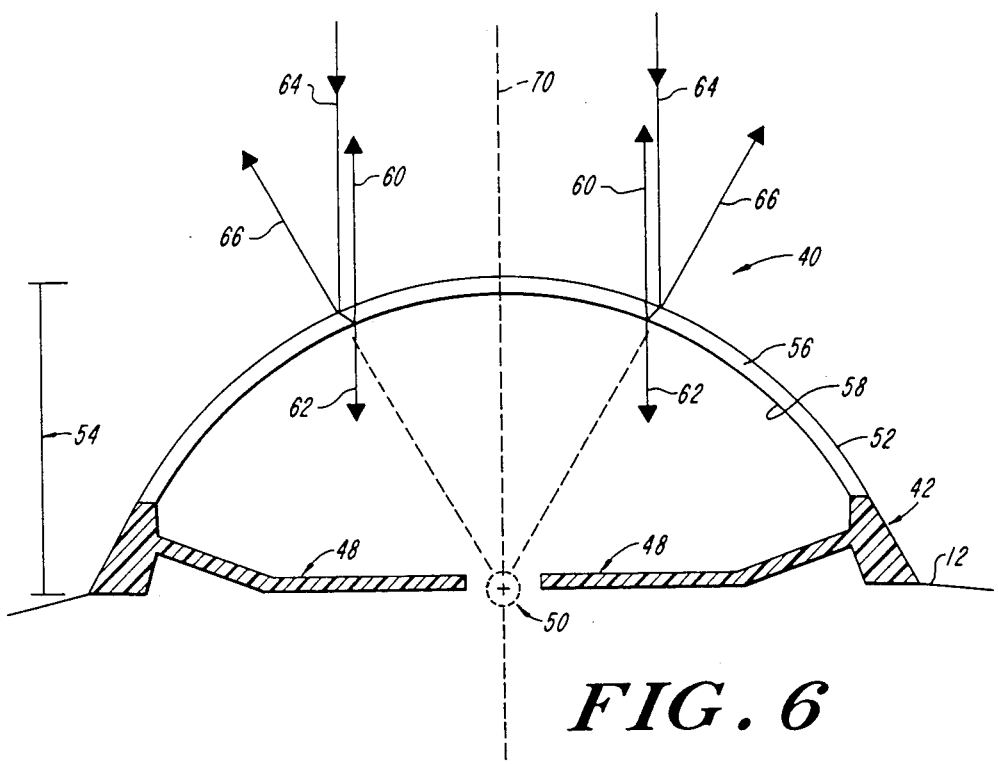
FIG. 6 is a sectional elevational view of the embodiment in FIG. 3.

The construction of the beam splitter is shown in FIG. 6. The beam splitter 40 is a coated, partially reflecting convex mirror having a radius of curvature of front surface 52 which is equal to twice the distance 54 from the apex of the surface 52 to the corneal surface 12 when the beam splitter rests on the corneal surface. The thickness of the curved element 56 is small and the curvature of the inner surface 58 is parallel to that of front surface 52. Thin wall construction and optical coatings on the surfaces 52 and 58 facilitate partial reflection at the front surface 52 and undeviated, minimal refraction between the two surfaces 52 and 58. The optical coating at the surface 58 minimizes secondary reflections 60. A partial-reflecting coating on the front surface 52 allows a refracted portion 62 of the incident ray 64 to pass through the lens so as to continue towards the interior of the eye. This thin-film coating at surface 52 is optimized for the wavelength of the incident collimated light beam.

In use, the patient is asked to fixate on a collimated point source 16 (FIG. 1). The eye of the patient thereby fixates such that the axis from the point source to the fovea 14 of the eye passes through the corneal surface 12 at a point of intersection termed herein the visual vertex 18. The beam splitter is moved on the corneal surface until the optical axis 70 of the beam splitter 40 merges with the visual axis 10 of the fixated eye. The secondary focus 50 thereupon superimposes with the visual vertex 18. Upon coincident alignment of the optical axis 70 and visual axis 10, the reflected rays 66 appear to emanate exactly from the visual vertex. The refracted rays 62 pass through the corneal surface 12 to the retina and fovea, thus allowing the patient to continue fixation upon the point source 16.

Proper positioning occurs only while the patient fixates on the point source 16 and the practitioner positions the beam splitter 40 to achieve a point source image on the corneal surface. The appearance of a point source image indicates that several optical axes are merged. The visual axis of the patient merges with the visual axis of the practitioner, which is merged with the optical axis of the viewing instrument and the incident and reflected rays of the point source 16. The point source image appearing at the secondary focus 50 is accurately superimposed on the visual vertex 18.

It is only at the moment of proper positioning, while viewing the corneal surface 12 and the beam splitter 40, that the practitioner discerns an abrupt appearance of the point source virtual image within the area defined by the radial spokes 48. The practitioner immediately impresses the corneal surface with the spoke pattern of the device 40. After removing the device from the corneal surface, the practitioner finds the epithelium of the corneal surface to be thereby marked with radial indentations which show the exact location of the visual vertex. The impression of the radial spokes remains until the epithelial cells regain their naturally smooth orientation. If the surgeon wishes the markings on the cornea to be longer-lasting than the indentations caused by relatively blunt spokes or bezel patterns, the indentations may be made more evident and long-lasting if the spokes and other marking parts of the bezel are made sufficiently sharp to create very fine, linear disruptions of the epithelium, rather than mere indentations.

It will be appreciated that the invention can be readily implemented. The viewing instrument 20 is common to many ophthalmological clinic, laboratory, and operating rooms. It may be easily and quickly equipped with a variety of light sources 22 which are well collimated and optimized for the fiber optic link 24 and beam splitter 28. Alternatively, the coupler 26, source 22, and link 24 can be replaced with a single coupler with integral LED or small solid-state laser and collimating optics.

The viewing apparatus 20 allows the practitioner a hands-free, close-up view of the corneal surface. The positioning of the beam splitter 40 can thereby be accomplished with swift and complete control by the practitioner and with minimal discomfort or distraction to the patient. The magnifying power of the viewing system allows the use of a low-intensity source 22, and because the beam splitter 40 can be positioned without occluding the visual axis, the patient can comfortably maintain fixation on the point source. The patient, while under topical anesthesia, does not notice the impression of the radial spokes.

The beam splitter can be formed as one piece from molded plastic. Even with the necessary dimensions and reflective coatings, the device can be manufactured at sufficiently low cost to be disposable. The device can be fabricated in an inexpensive assortment of devices, each optimized for a particular operation or procedure, and packaged as a sterile item.

The alignment and pattern of the radial spokes 48 can be optimized to suit specific applications. For instance, those for radial keratotomy might have the central circle of the desired diameter, and include small radial extensions to mark the positions of the meridians to be cut. A variety of beam splitters can be prepared for indicating the requisite number of incisions for any surgical procedure. Spoke alignment for epikeratophakia could be prepared in the larger diameters needed for that operation. The bezel 42 can have enough flexibility to permit a tiny, central marking area to press against the corneal surface, along with larger, peripheral marking circle then to be pressed onto the epithelium, regardless of the steepness of the slope of the corneal surface.

As described above, the invention can also be implemented for direct visualization of an impinging narrow beam with the cornea without the beam splitter 40. This embodiment can be practiced with the viewing apparatus of FIG. 2 wherein the narrow light beam is directed along the axis 30 into the eye of the patient. The intersection of the incident beam with the corneal surface is viewed by the practitioner in the other optical channel than the one containing the incident beam, which is off-axis by a small amount from the illuminated side of the instrument. The scattering of the impinging light beam in its path through the corneal tissue provides sufficient light to be viewed through the nonilluminated side of the viewing instrument. The wavelength of the incident narrow beam is determined to provide an intended degree of scattering for each viewing. Preferably, the light beam can be provided by a solid state laser in the blue/green or blue wavelength range. Marking of the visual vertex can be accomplished with any suitable marking apparatus. Alternatively, the corneal surface can be coated with a fluorescent dye which will fluoresce upon activation by the impinging light beam. The fluorescent radiation can be viewed through the viewing instrument either onaxis with the incident beam or off-axis through the nonilluminated side of the instrument to detect the visual vertex.

Other modifications and alternative implementations may occur to those skilled in the art without departing from the spirit and true scope of the invention. Accordingly, the invention is not to be limited by what has been particularly shown and described except as indicated in the appended claims.

What is claimed is:

1. A method for use with a viewing instrument having first and second optical channels having first and second optical axes, respectively, to locate a visual vertex of an eye fixated on a light source, a visual axis being defined between the fovea of the fixated eye and the light source wherein the visual vertex is the intersection point of the visual axis with the front corneal surface of the fixated eye, comprising the steps of:
   producing a collimated light beam via the light source;
   projecting the collimated light beam produced by the light source along the first optical axis of the first optical channel of the viewing instrument wherein the collimated light beam is coaxial with the visual axis of the eye fixated on the light source;
   viewing passage of the collimated light beam into and through the corneal tissue of the fixated eye along the second optical axis of the second optical channel of the viewing instrument, the second optical axis being slightly displaced off-axis from the first optical axis and the visual axis coaxial therewith; and
   noting scattering of the collimated light beam passing through the corneal tissue of the fixated eye to locate the visual vertex as the point of intersection of the visual axis with the front corneal surface.

2. The method of claim 1 wherein said step of producing a collimated light beam further comprises producing a collimated light beam via the light source external from the viewing instrument and wherein said step of projecting the collimated light beam along the first optical axis further comprises
   coupling the collimated light beam from the external light source to the first optical channel of the viewing instrument; and
   directing the collimated light beam along the first optical axis of the first optical channel of the viewing instrument.

3. The method of claim 2 wherein said step of producing a collimated light beam further comprises producing a collimated light beam of predetermined wavelength from a low power laser external from the viewing instrument and wherein the low power laser is the external light source.

4. The method of claim 2 wherein said step of producing a collimated light beam further comprises producing a collimated light beam of predetermined wavelength from a light emitting diode external from the viewing instrument and wherein the light emitting diode is the external light source.

5. The method of claim 2 wherein said step of coupling further comprises coupling the collimated light beam from the external light source through a fiberoptic path to the viewing instrument.

6. The method of claim 5 wherein said directing step further comprises directing the collimated light beam from the fiberoptic path to a beam splitter in the first optical channel to direct the collimated light beam along the first optical axis of the viewing instrument.

7. A beam splitter for use in combination with a viewing instrument having an optical axis and a light source producing a collimated light beam coincident with the optical axis of the viewing instrument to locate a visual vertex of an eye fixated on the light source, a visual axis for the collimated light beam being defined between the fovea of the fixated eye and the light source wherein the visual vertex is the intersection point of the visual axis with the front corneal surface of the fixated eye, comprising:
   an annular base portion for engagement with the front corneal surface of the fixated eye;
   a curved mirror centrally disposed on said annular base portion distal to the front corneal surface of the fixated eye, and wherein said curved mirror is partially reflective and partially transmissive to the collimated light beam incident thereon;
   said curved mirror and said base portion in combination defining an optical axis for said beam splitter, and wherein said curved mirror is structurally configured to cause the collimated light beam incident thereon to form a virtual image of the light source on the front corneal surface of the fixated eye at the visual vertex when said optical axis of said beam splitter is coincident with the visual axis of the fixated eye; and
   means for moving said beam splitter on the front corneal surface of the fixated eye to align said optical axis of said beam splitter with the visual axis of the fixated eye thereby causing
   the collimated light beam to form the virtual image of the light source on the front corneal surface of the fixated eye at the visual vertex and wherein the virtual image of the light source is located via the viewing instrument.

8. The beam splitter of claim 7 wherein said means for moving said beam splitter on the front corneal surface of the fixated eye is a handle extending outwardly from said annular base portion.

9. The beam splitter of claim 8 wherein said curved mirror is a convex mirror having a front surface distal to the front corneal surface of the fixated eye and an inner surface parallel to said front surface and inwardly disposed therefrom by a small predetermined distance and wherein said front surface has a thin, partially reflecting coating thereon to allow a refracted portion of the collimated light beam to pass through said convex mirror to form the virtual image at the visual vertex of the front corneal surface of the fixated eye when the optical axis thereof is aligned with said optical axis of said beam splitter.

10. The beam splitter of claim 9 wherein said front surface of said beam splitter has an apex disposed a predetermined distance above the front corneal surface of the fixated eye and a radius of curvature twice said predetermined distance.

11. The beam splitter of claim 7 further comprising means for marking the front corneal surface of the fixated eye by pressing said beam splitter to form indentations in the front corneal surface to thereby locate the virtual image formed at the visual vertex.

12. The beam splitter of claim 7 wherein said annular base portion includes a plurality of scuppers formed through said annular base portion for drainage of liquid from within said beam splitter.

13. The beam splitter of claim 7 wherein said annular base portion is a bezel and wherein said beam splitter further comprises a plurality of spokes inwardly extending from said bezel and having inner tips defining a secondary focus of of said beam splitter wherein the virtual image is formed.

14. A method for use in combination with a viewing instrument having an optical axis and a light source producing a collimated light beam coaxial with the optical axis of the viewing instrument to locate a visual vertex of an eye, comprising the steps of:

introducing the collimated light beam into the eye fixated on the light source, to define a visual axis between the fovea of the fixated eye and the fixated eye wherein the visual vertex is the intersection point of the visual axis with the front corneal surface of the fixated eye;

positioning a beam splitter including a bezel for supporting said beam splitter on the front corneal surface, a convex mirror integral with said bezel, an optical axis, and a plurality of spokes projecting radially inwardly of said bezel to define a secondary focus on the front corneal surface in a position wherein the collimated light beam is intercepted by the convex mirror which is partially reflective and partially transmissive to the collimated light beam;

moving said beam splitter along the front corneal surface of the fixated eye until a virtual image of the light source appears in said secondary focus defined by said plurality of spokes indicating that said optical axis of said beam splitter is coincident with the visual axis of the fixating eye and that the virtual image is superimposed upon the visual vertex of the fixated eye; and marking the front corneal surface by pressing on said beam splitter to cause said plurality of spokes to form indentations in the front corneal surface to define the point on the front corneal surface wherein the virtual image is seen via the viewing instrument.

15. A method for use with a viewing instrument having first and second optical channels having first and second optical axes, respectively, to mark a visual vertex of an eye fixated on a light source, a visual axis being defined between the fovea of the fixated eye and the light source wherein the visual vertex is the intersection point of the visual axis with the front corneal surface of the fixated eye, comprising the steps of:

projecting along the first optical axis of the first optical channel of the viewing instrument a collimated light beam produced by the light source into the eye fixated on the light source wherein the collimated light beam is coaxial with the visual axis;

viewing passage of the collimated light beam into and through the corneal tissue of the fixated eye along the second optical axis of the second optical channel of the viewing instrument, the second optical axis being slightly displaced off-axis from the first optical axis and the visual axis coaxial therewith;

noting scattering of the collimated light beam passing through the corneal tissue of the fixated eye to locate the visual vertex as the point of intersection of the visual axis with the front corneal surface; and marking the front corneal surface by scoring thereof with a sharp instrument to denote the point of intersection of the visual axis with the front corneal surface.

16. A beam splitter for use in combination with a viewing instrument having an optical axis and a light source producing a narrow collimated light beam coincident with the optical axis to detect and mark a visual vertex upon an eye fixated on the light source, a visual axis for the narrow collimated light beam being defined between the fovea of the fixated eye and the light source wherein the visual vertex is the doing of intersection of the visual axis with the front corneal surface of the fixated eye, comprising:

a generally circular bezel having an upper edge and a lower edge for support of beam splitter on the front corneal surface of the fixated eye;

means for manipulating said generally circular bezel along the front corneal surface of the fixated eye;

means, integral with said generally circular bezel and extending radially inwardly therefrom, for defining a secondary focus and for marking the fixated eye by indenting the front corneal surface of the fixated eye upon application of pressure to said beam splitter; and a central convex portion integral with said upper edge of said generally circular bezel and wherein said central convex portion is partially reflective and partially transmissive to the narrow collimated light beam from the light source;

said generally circular bezel and said central convex portion in combination having an optical axis; and wherein said optical axis of said beam splitter is merged with the visual axis of the fixated eye to detect the visual vertex thereof by manipulation of said beam splitter along the front corneal surface of the fixated eye via said manipulating means to cause a virtual image of the light source to appear at said secondary focus of said defining means, the virtual image being accurately superimposed on the visual vertex of the fixated eye, and wherein the visual vertex is marked upon the front corneal surface of the fixated eye with said marking means by applying pressure to said beam splitter to cause indentations in the front corneal surface of the fixated eye defining said secondary focus.

17. The beam splitter of claim 16 wherein said central convex portion has inner and front parallel convex surfaces defining a thin convexly curved mirror therebetween and wherein optical coatings are applied to said inner and front parallel to convex surfaces to provide reflection at said front convex surface and undeviated minimal refraction of the narrow collimated light beam between said inner and front parallel convex surfaces.

18. The instrument of claim 16 wherein the beam splitter includes a central portion having inner and outer parallel surfaces defining a thin curved element and one or more optical coatings to provide partial reflection at the front surface and undeviated minimal refraction between the two parallel surfaces.

19. The beam splitter of claim 18 wherein said optical coating on the said front convex surface is optimized for the wavelength of the narrow collimated light beam.

20. A method for use with a viewing instrument having first and second optical channels having first and second optical axes, respectively, to locate a visual vertex of an eye fixated on a light source, a visual axis being defined between the fovea of the fixated eye and the light source wherein the visual vertex is the intersection point of the visual axis with the front corneal surface of the fixated eye, comprising the steps of:

coating the front corneal surface of the fixated eye with a fluorescent dye with fluoresces when activated by light energy;

producing a collimated light beam via the light source having sufficient light energy to activate the fluorescent dye;

projecting the collimated light beam produced by the light source along the first optical axis of the first optical channel of the viewing instrument coaxially with the visual axis to impinge upon the front corneal surface of the fixated eye causing the fluorescent dye to fluoresce at the visual vertex of the fixated eye; and viewing the fluorescent radiation from the visual vertex of the fixated eye through the second optical axis of the second optical channel of the viewing instrument to thereby locate the visual vertex of the fixated eye.

* * * * *

UNITED STATES PATENT AND TRADEMARK OFFICE
CERTIFICATE OF CORRECTION

PATENT NO. : 4,799,784

DATED : January 24, 1989

INVENTOR(S) : Aran Safir

It is certified that error appears in the above-identified patent and that said Letters Patent is hereby corrected as shown below:

Column 1, line 52, "needed" should read --needle--

Column 6, line 60, "onaxis" should read --on axis--

Column 8, line 62, "of of" should read --of--

Column 9, lines 3-4, "between the fovea of the fixated eye and the fixated eye" should read --between the fovea of the fixated eye and the light source--

Column 10, line 38, "parallel to convex" should read --parallel convex--

Column 10, line 61, "dye with" should read --dye which--

Signed and Sealed this

Twenty-eighth Day of August, 1990

Attest:

HARRY F. MANBECK, JR.

*Attesting Officer*     *Commissioner of Patents and Trademarks*